(12) United States Patent
Euvrard et al.

(10) Patent No.: US 7,927,100 B2
(45) Date of Patent: Apr. 19, 2011

(54) DEVICE FOR PROTECTING THE HEAD OF A DENTAL HANDPIECE AND SEALED PACKAGING FOR AN INSERT EQUIPPED WITH SAID DEVICE

(75) Inventors: Hubert Euvrard, Besancon (FR); Jean-Pierre Ouhayoun, Dizy (FR)

(73) Assignee: Micro Mega International Manufactures (Societe Anonyme), Besancon (FR)

( * ) Notice: Subject to any disclaimer, the term of this patent is extended or adjusted under 35 U.S.C. 154(b) by 156 days.

(21) Appl. No.: 11/816,707

(22) PCT Filed: Nov. 28, 2005

(86) PCT No.: PCT/FR2005/002945
§ 371 (c)(1),
(2), (4) Date: Oct. 19, 2007

(87) PCT Pub. No.: WO2006/090021
PCT Pub. Date: Aug. 31, 2006

(65) Prior Publication Data
US 2008/0213721 A1 Sep. 4, 2008

(30) Foreign Application Priority Data
Feb. 24, 2005 (FR) ...................................... 05 01863

(51) Int. Cl.
*A61C 1/16* (2006.01)
(52) U.S. Cl. ........................................................ 433/116
(58) Field of Classification Search ................... 433/77, 433/116, 125; 206/63.5, 368, 369
See application file for complete search history.

(56) References Cited

U.S. PATENT DOCUMENTS

| 4,723,912 | A | | 2/1988 | Nieusma et al. | |
|---|---|---|---|---|---|
| 4,741,326 | A | * | 5/1988 | Sidall et al. | 600/123 |
| 5,267,860 | A | * | 12/1993 | Ingram et al. | 433/116 |
| 2002/0112971 | A1 | * | 8/2002 | Pieroni et al. | 206/63.5 |
| 2002/0178566 | A1 | * | 12/2002 | Reich | 29/426.5 |
| 2003/0162145 | A1 | | 8/2003 | Masterman | |
| 2005/0282102 | A1 | * | 12/2005 | Kert | 433/29 |

* cited by examiner

*Primary Examiner* — Cris L Rodriguez
*Assistant Examiner* — Eric Rosen
(74) *Attorney, Agent, or Firm* — Egbert Law Offices PLLC

(57) ABSTRACT

The invention relates to a protective device for dental equipment of the type including a straight handpiece or a contra-angle. The dental equipment is formed by a body enclosing a motor unit and/or members for transmitting movement and a tool-holder head bearing a tool. The protective device is a sleeve that has the general form of a glove finger, with an opening at one end and a closed base at the other end. The invention also relates to a sealed packaging for an insert formed by a tool-holder head bearing the tool and equipped with the protective device.

6 Claims, 2 Drawing Sheets

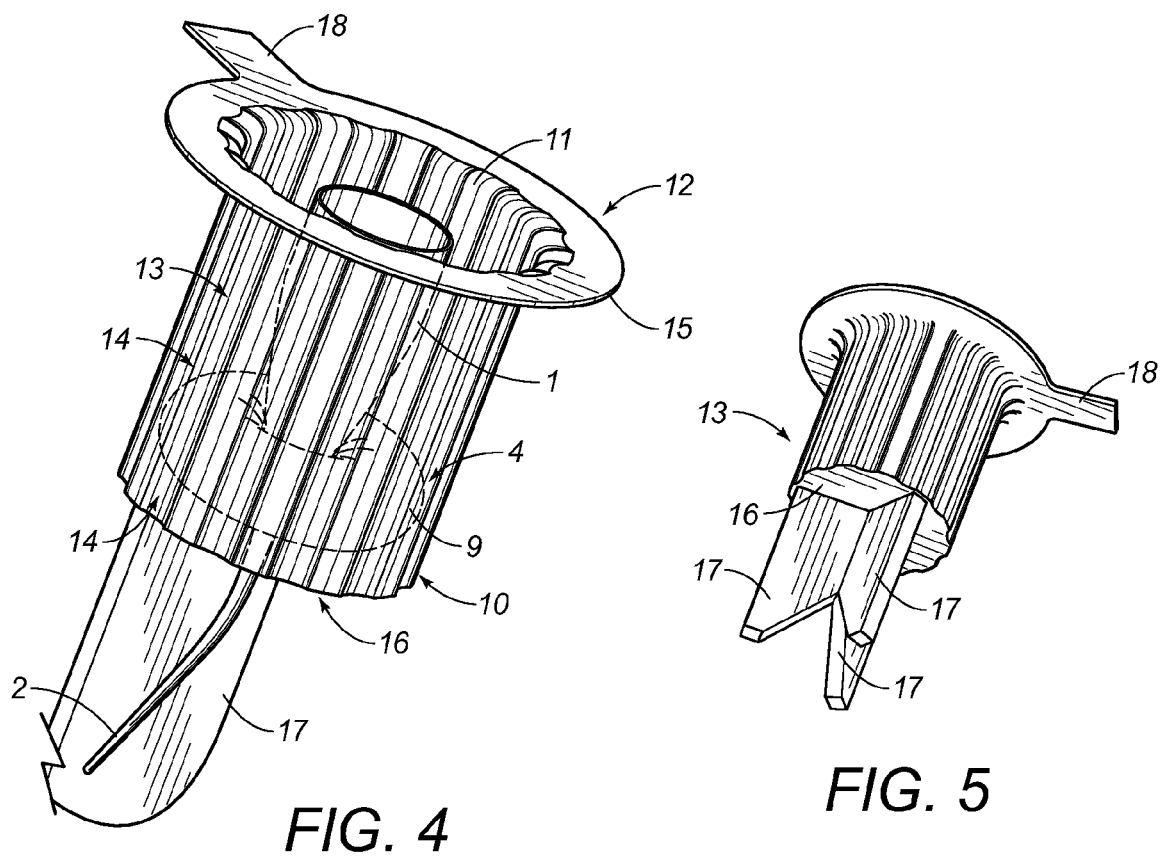
FIG. 4
FIG. 5
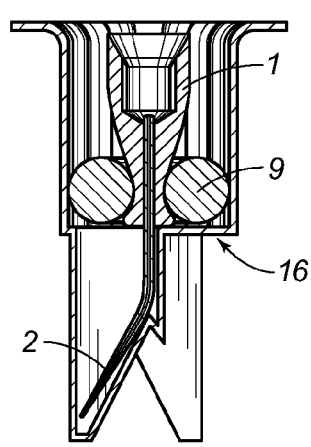
FIG. 6
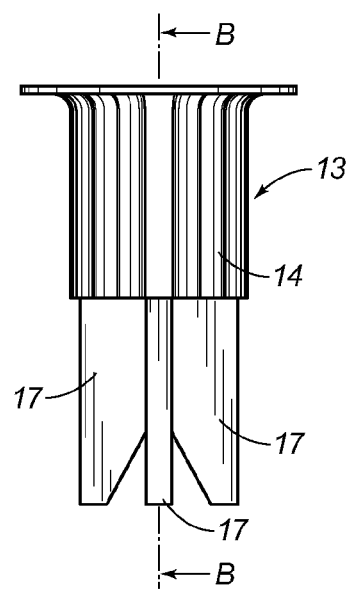
FIG. 7

DEVICE FOR PROTECTING THE HEAD OF A DENTAL HANDPIECE AND SEALED PACKAGING FOR AN INSERT EQUIPPED WITH SAID DEVICE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a device for protecting the head of a dental handpiece.

2. Description of Related Art Including Information Disclosed Under 37 CFR 1.97 and 37 CFR 1.98

It is an object of the invention to make available a simple and easy-to-use device for protecting the handpiece or contra-angle while carrying out work in the mouth.

Another object of the invention is to design a sterile package for an insert for a straight handpiece or contra-angle which provides the dentist with sterilized and optionally disposable inserts and which is used to safely fit the insert that it contains on the handpiece or contra-angle.

In the text that follows, insert will designate an assembly formed by a tool-holder head and by a periodontal tool, for example, mounted on the latter. This assembly is able to be engaged by screwing, snap-fitting or the like onto a handpiece or contra-angle.

BRIEF SUMMARY OF THE INVENTION

These objects are achieved by the invention, which involves a device for protecting dental equipment of the type composed mainly of a straight handpiece or a contra-angle, which are formed by a body enclosing a motor unit and/or members for transmitting movement and a tool-holder head bearing a tool. The protective device is a sleeve having the general form of a glove finger, with an opening at one end and a closed base at the other end.

The sleeve is preferably made of flexible material that can be rolled up on itself, or the sleeve is made of a material that can be folded in an accordion shape.

In its initial position, the sleeve is preferably compacted or rolled up externally on itself and can be placed on the distal end of the tool-holder head. Its closed base is traversed by the tool, and, in the position of use, the sleeve is deployed or unrolled on the head and on at least part of the body of the handpiece or contra-angle.

The invention also relates to a disposable assembly for dental equipment, composed of an insert and its sealed packaging, said packaging being formed by a package with an envelope of generally tubular shape. This envelope is dimensioned and open at one end in order to permit introduction of an insert equipped with a protective sleeve according to the invention.

At its distal end, the head of the insert preferably has an annular depression terminated by an annular bulge serving for the positioning of a bead formed by the rolled-up or compacted sleeve.

In addition, the external diameter of the bead of the rolled-up or compacted sleeve is such that said bead comes into contact with the inner wall of the envelope or with the bases of the ribs of said envelope, if the latter comprises such ribs, in such a way that the compacted sleeve transmits the forces of engagement of the insert or tool on the equipment. The forces are transmitted by the friction between the material of the sleeve and that of the packaging, this friction being able to be increased by surface shapes and/or surface states.

The packaging is preferably characterized by an envelope which is closed, at its end opposite the one with the collar, by a flat base and at least one flat and hollow sheath, the inner cavity of which is able to receive the tool.

BRIEF DESCRIPTION OF THE SEVERAL VIEWS OF THE DRAWINGS

The invention will be better understood from the following description in which reference is made to the attached figures.

FIG. 4 shows a perspective view of a packaged assembly of the present invention.

FIG. 5 shows a perspective view of another packaged assembly of the present invention.

FIGS. 6 and 7 show a cross-sectional view and an elevation view, respectively of the packaged assembly shown in FIG. 5, the cross-section being taken across line B-B in FIG. 7.

DETAILED DESCRIPTION OF THE INVENTION

By way of an example of the application of the invention, the figures show a disposable insert formed by a head (1) bearing a curved curette (2) mounted on a straight handpiece (3).

Figure 1:
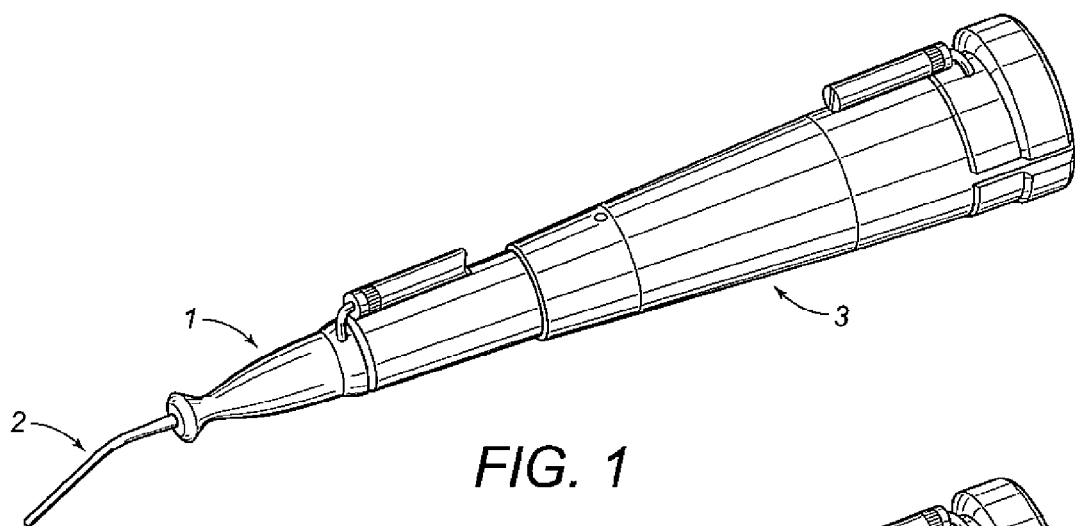
FIG. 1 shows a perspective view of a straight hand-piece on which an insert with curved curette is mounted, cited by way of example of a possible application of the invention.
Figure 2:
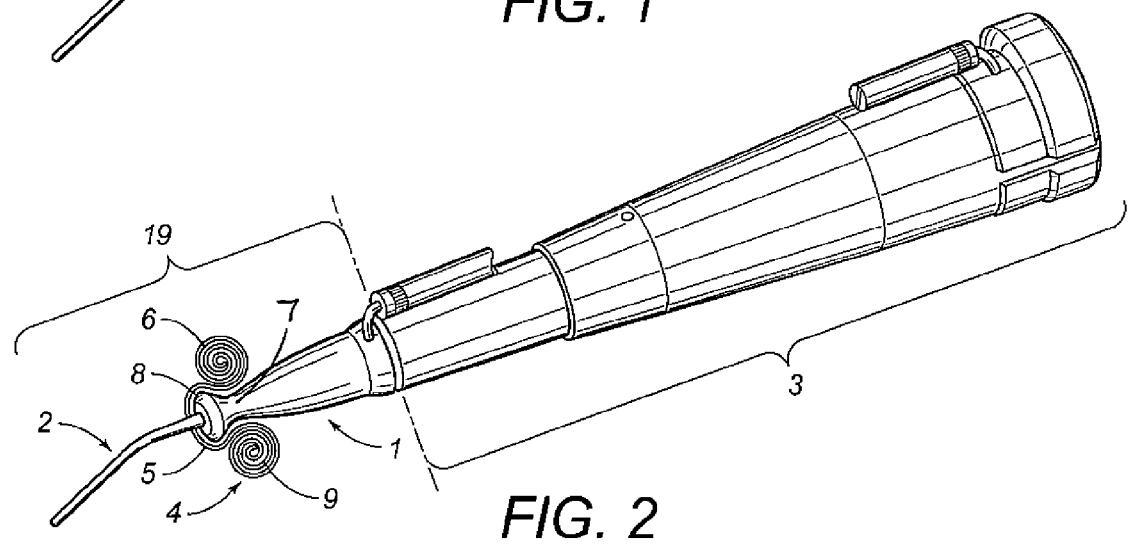
FIG. 2 shows another perspective view of the handpiece and the insert from FIG. 1, depicting a protective sleeve according to the invention in the initial rolled-up position.
Figure 3:
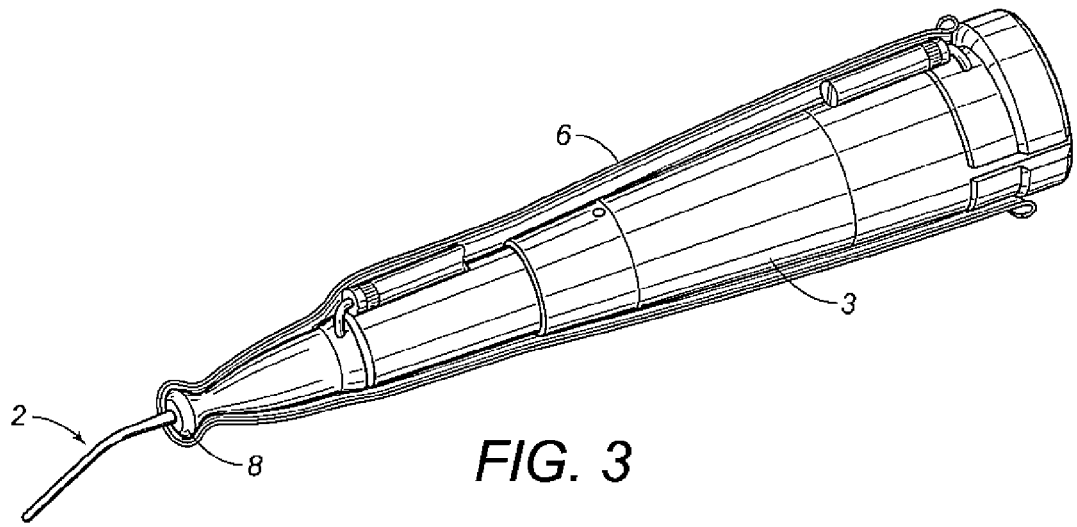
FIG. 3 shows still another perspective view of the handpiece and the insert from FIG. 1, with the protective sleeve unrolled to its full extent.

FIGS. 2 and 3 show the principle of the use of a protective sleeve (4) according to the invention, made of a flexible and rollable material, for example latex, the general form of which is that of a glove finger, with an opening (6) at one end and a closed base (5) at the other end.

In the initial position (FIG. 2), the sleeve is rolled up externally on itself and placed on the distal end of the tool-holder head, and its closed base (5) is traversed by the tool (2).

To make it easier to keep the rolled-up sleeve in place, the head (1) preferably has, at its distal end, an annular depression (7) terminated by an annular bulge (8) used for positioning the bead (9) formed by the rolled-up sleeve.

To protect the entire equipment during dental work, it suffices to unroll the sleeve along the head and body of the equipment, as is shown in FIG. 3. The unrolled sleeve preferably covers the entire length of the equipment and is held in place thereon by the elasticity of the material.

According to variants not shown here, sleeves made of other materials with different modes of deployment and compacting can be provided, for example a sleeve that is folded in an accordion shape in its initial compacted form and that can be unfolded along the length of the equipment.

The protective sleeve according to the invention can be supplied individually and the dentist can fit it, in its initial compacted form, onto any type of dental equipment, after which it is deployed along the length of said equipment in order to at least partially cover the latter, and at least the junction area between the head and the body of the equipment.

This protective sleeve is preferably compacted in its initial form and is engaged on the head of an insert, which is optionally disposable, the whole assembly being packaged and sterilized in a package (10) which is closed in a sealed manner by a cover (11).

The packaging (12) shown by way of example in FIG. 4 is composed of a package (10), preferably of transparent material, formed by an envelope (13) of generally tubular shape presenting longitudinal ribs (14) that make it easier to grip, this envelope being dimensioned and open at one end in order to permit introduction of an insert equipped with a protective sleeve compacted in the initial position, said end being bordered by a flat collar (15) on which a cover (11) for closing the cylindrical envelope (13) can be welded. The envelope is also closed at its other end on the one hand by a flat base (16) and on the other hand by a flat and hollow sheath (17), said sheath (17) being designed to receive the curette or any other tool (2) of the insert.

In the traditional manner, the cover (11) comprises a tab (18) that can be gripped in order to pull off said cover.

According to a design variant shown in FIGS. 5 to 7, the envelope (13) is continued by three sheaths (17) arranged radially at 60° and serving as feet on which the package can be set down vertically with the cover at the top. They can also help for gripping and/or turning the packaging in order to screw or engage the insert on the contra-angle or handpiece.

The external diameter of the bead (9) of the rolled-up or compacted sleeve is preferably such that said bead comes into contact with the inner wall of the envelope (13) or with the bases of the ribs of said envelope, if the latter comprises such ribs, in such a way that the compacted sleeve ensures transmission of the forces of engagement of the insert or tool on the apparatus. This force transmission is achieved by the friction between the material of the sleeve and that of the packaging, this friction being able to be increased by surface forms and/or surface states.

The form of the package that has just been described is suitable for an insert bearing a curved tool and that can be fitted on a straight handpiece.

Of course, the principle of the packaging according to the invention can be transposed to inserts with a straight tool for contra-angles, by modifying the form of the package.

In all cases, the packages containing different types of tools are delivered in a sterilized format to the dentist. The latter chooses the tool that is required, tears off the cover with one hand, while holding the package in the other hand, then screws or snap-fits the insert onto the equipment without touching it. The maneuver is therefore done without risk of contamination of the tool and without risk of injury to the dentist.

We claim:

1. A disposable assembly for a dental instrument in which the dental instrument has a handpiece formed by a body enclosing a motor unit, the disposable assembly comprising:
   an insert having a tool-holder head bearing a tool at an end thereof, said tool-holder head having a protective sleeve compacted upon itself and suitable for extending over the handpiece, said protective sleeve having a closed base residing directly against said end of said tool-holder head and through which said tool passes; and
   a sealed packaging having an envelope of a generally tubular shape, said envelope having an opening at one end, said insert being received into said envelope through said one end, said envelope being bordered by a collar at said one end, said collar having a cover welded thereto so as to extend over the opening at said one end, said tool-holder head having an annular depression formed adjacent an end thereof, said tool-holder head having an annular bulge at said end thereof, said protective sleeve being rolled up or compacted so as to have a shape of a bead, said bead received over said annular depression and against said annular bulge.

2. The disposable assembly of claim 1, said bead having an outer diameter in contact with an inner wall of said envelope.

3. The disposable assembly of claim 1, said sleeve being of a flexible material that can be rolled up upon itself.

4. The disposable assembly of claim 1, and said sleeve being formed of a material having an accordion shape.

5. The disposable assembly of claim 1, said sleeve being of a latex material.

6. The disposable assembly of claim 1, said envelope having a flat base and at least one flat and hollow sheath extending therefrom at an end of said envelope opposite said collar, said sheath receiving said tool therein.

* * * * *